(12) United States Patent
Thill et al.

(10) Patent No.: US 9,180,002 B2
(45) Date of Patent: Nov. 10, 2015

(54) STENTLESS SUPPORT STRUCTURE

(75) Inventors: Gary A. Thill, Vadnais Heights, MN (US); Robert Foster Wilson, Roseville, MN (US); John Gainor, White Bear Township, MN (US); Christopher M. Banick, Minnetrista, MN (US)

(73) Assignee: HLT, Inc., Maple Grove, MN (US)

( * ) Notice: Subject to any disclaimer, the term of this patent is extended or adjusted under 35 U.S.C. 154(b) by 253 days.

(21) Appl. No.: 13/458,023

(22) Filed: Apr. 27, 2012

(65) Prior Publication Data

US 2012/0209370 A1    Aug. 16, 2012

Related U.S. Application Data

(63) Continuation of application No. 11/443,814, filed on May 30, 2006.

(60) Provisional application No. 60/685,349, filed on May 27, 2005, provisional application No. 60/709,595, filed on Aug. 18, 2005, provisional application No. 60/685,433, filed on May 27, 2005.

(51) Int. Cl.
*A61F 2/24* (2006.01)
*A61F 2/90* (2013.01)
(Continued)

(52) U.S. Cl.
CPC ............... *A61F 2/2418* (2013.01); *A61F 2/06* (2013.01); *A61F 2/2436* (2013.01); *A61F 2/90* (2013.01); *A61F 2/95* (2013.01); *A61F 2220/0075* (2013.01); *A61F 2230/0067* (2013.01); *A61F 2250/0039* (2013.01)

(58) Field of Classification Search
CPC ............... A61F 2/2418; A61F 2/2412; A61F 2230/0054; A61F 2220/0016
USPC ............... 623/1.24, 1.26, 1.51, 1.53, 2.18
See application file for complete search history.

(56) References Cited

U.S. PATENT DOCUMENTS

| 5,669,931 | A | * | 9/1997 | Kupiecki et al. ............... 606/191 |
| 6,016,810 | A | | 1/2000 | Ravenscroft |
| 6,126,686 | A | | 10/2000 | Badylak et al. |

(Continued)

FOREIGN PATENT DOCUMENTS

DE    102005052628 A1    10/2007

OTHER PUBLICATIONS

Japanese Patent Office, Office Action mailed Sep. 28, 2011 in Japanese Patent Application No. JP2008-513838, 7 pages.

(Continued)

*Primary Examiner* — Thomas J Sweet
*Assistant Examiner* — Tiffany Shipmon
(74) *Attorney, Agent, or Firm* — Inskeep IP Group, Inc.

(57) ABSTRACT

A stentless support structure capable of being at least partly assembled in situ. The support structure comprises a braided tube that is very flexible and, when elongated, becomes very long and very small in diameter, thereby being capable of placement within a small diameter catheter. The support structure is preferably constructed of one or more thin strands of a super-elastic or shape memory material such as Nitinol. When released from the catheter, the support structure folds itself into a longitudinally compact configuration. The support structure thus gains significant strength as the number of folds increase. This radial strength obviates the need for a support stent. The support structure may include attachment points for a prosthetic valve.

20 Claims, 18 Drawing Sheets

(51) Int. Cl.
*A61F 2/06* (2013.01)
*A61F 2/95* (2013.01)

(56) References Cited

U.S. PATENT DOCUMENTS

| | | | |
|---|---|---|---|
| 6,287,335 B1 * | 9/2001 | Drasler et al. | 623/1.28 |
| 6,592,614 B2 * | 7/2003 | Lenker et al. | 623/1.13 |
| 7,329,279 B2 | 2/2008 | Haug et al. | |
| 2002/0032481 A1 * | 3/2002 | Gabbay | 623/2.11 |
| 2002/0128703 A1 * | 9/2002 | Ravenscroft | 623/1.13 |
| 2004/0220664 A1 | 11/2004 | Chobotov | |
| 2004/0260333 A1 | 12/2004 | Dubrul et al. | |
| 2005/0137702 A1 * | 6/2005 | Haug et al. | 623/2.38 |
| 2005/0222674 A1 * | 10/2005 | Paine | 623/1.24 |
| 2005/0283231 A1 * | 12/2005 | Haug et al. | 623/2.11 |
| 2009/0076598 A1 | 3/2009 | Salahieh et al. | |
| 2009/0222076 A1 | 9/2009 | Figulla et al. | |

OTHER PUBLICATIONS

IP Australia, Notice of Acceptance mailed Sep. 15, 2011 in Australian Patent Application No. AU2006251938, 3 pages.
State Intellectual Property Office, P.R. China, First Office Action mailed Nov. 27, 2009 in Chinese Patent Application No. CN201010533068.8, 4 pages.
IP Australia, Examiner's Report mailed Apr. 18, 2011 in Australian Patent Application No. AU2006251938, 2 pages.
United States Patent and Trademark Office, Final Office Action mailed Dec. 14, 2010 in U.S. Appl. No. 11/443,814, 10 pages.
United States Patent and Trademark Office, Final Office Action mailed Jul. 22, 2011 in U.S. Appl. No. 11/443,814, 9 pages.
United States Patent and Trademark Office, Office Action mailed Dec. 20, 2009 in U.S. Appl. No. 11/443,814, 7 pages.
State Intellectual Property Office, P.R. China, Examiner's Report mailed Nov. 27, 2009 in Chinese Patent Application No. CN200680027512.0, 6 pages.
United States Patent and Trademark Office, Office Action mailed Apr. 17, 2009 in U.S. Appl. No. 11/443,814, 7 pages.
United States Patent and Trademark Office, Final Office Action mailed Nov. 17, 2008 in U.S. Appl. No. 11/443,814, 10 pages.
United States Patent and Trademark Office, Office Action mailed Mar. 18, 2008 in U.S. Appl. No. 11/443,814, 10 pages.
WIPO, U.S. International Preliminary Examining Authority, International Preliminary Report on Patentability mailed Nov. 30, 2007 in International Patent Application No. PCT/US2006/021021, 7 pages.
WIPO, U.S. International Search Authority, International Search Report and Written Opinion mailed Sep. 5, 2007 in International Patent Application No. PCT/US2006/021021, 10 pages.

* cited by examiner

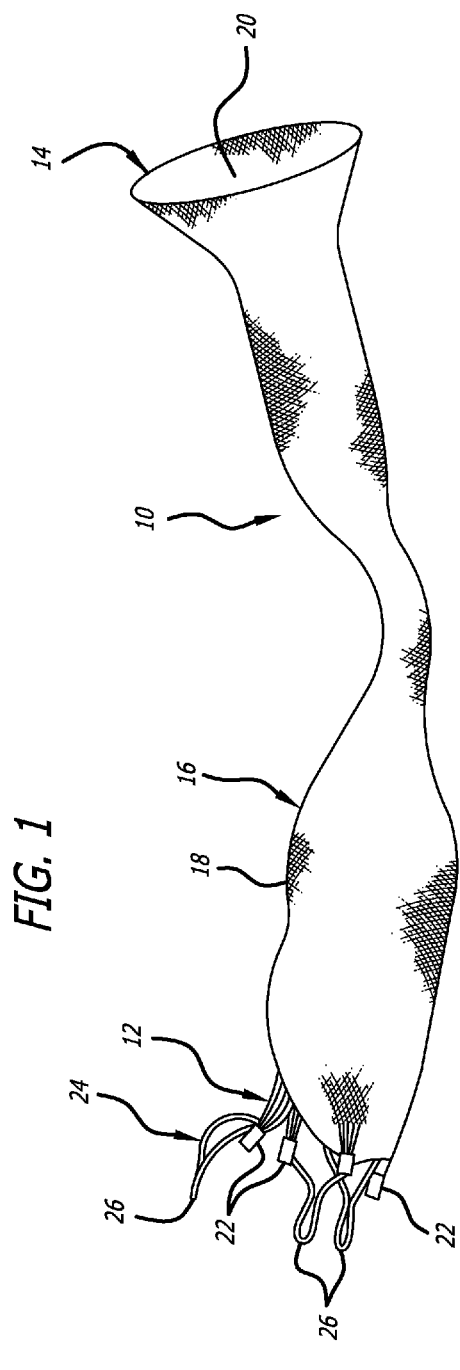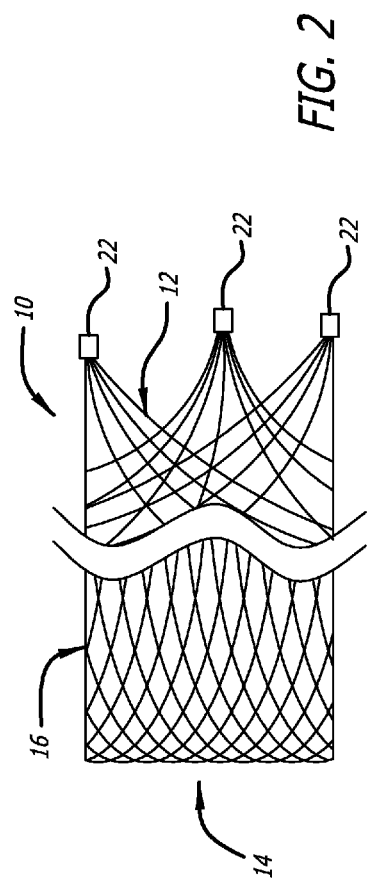
FIG. 1
FIG. 2

STENTLESS SUPPORT STRUCTURE

CROSS-REFERENCE TO RELATED DOCUMENTS

This application is a continuation of U.S. patent application Ser. No. 11/443,814 filed May 30, 2006 entitled Stentless Support Structure, which is related to and claims priority benefit of U.S. Provisional Patent Application Ser. No. 60/685,349, filed May 27, 2005, entitled Stentless Support Structure, by Wilson et al. and U.S. Provisional Patent Application Ser. No. 60/709,595, filed Aug. 18, 2005, entitled Stentless Support Structure by Wilson et al. These applications are also hereby incorporated by reference herein. This application also incorporates by reference U.S. patent application Ser. No. 11/442,371 entitled Intravascular Cuff filed by Applicant on May 30, 2006 and U.S. Provisional Patent Application Ser. No. 60/685,433, filed May 27, 2005, entitled Intravascular Cuff.

BACKGROUND OF THE INVENTION

There has been a significant movement toward developing and performing cardiovascular surgeries using a percutaneous approach. Through the use of one or more catheters that are introduced through, for example, the femoral artery, tools and devices can be delivered to a desired area in the cardiovascular system to perform many number of complicated procedures that normally otherwise require an invasive surgical procedure. Such approaches greatly reduce the trauma endured by the patient and can significantly reduce recovery periods. The percutaneous approach is particularly attractive as an alternative to performing open-heart surgery.

Valve replacement surgery provides one example of an area where percutaneous solutions are being developed. A number of diseases result in a thickening, and subsequent immobility or reduced mobility, of heart valve leaflets. Such immobility also may lead to a narrowing, or stenosis, of the passageway through the valve. The increased resistance to blood flow that a stenosed valve presents can eventually lead to heart failure and ultimately death.

Treating valve stenosis or regurgitation has heretofore involved complete removal of the existing native valve through an open-heart procedure followed by the implantation of a prosthetic valve. Naturally, this is a heavily invasive procedure and inflicts great trauma on the body leading usually to great discomfort and considerable recovery time. It is also a sophisticated procedure that requires great expertise and talent to perform.

Historically, such valve replacement surgery has been performed using traditional open-heart surgery where the chest is opened, the heart stopped, the patient placed on cardiopulmonary bypass, the native valve excised and the replacement valve attached. A proposed percutaneous valve replacement alternative method on the other hand, is disclosed in U.S. Pat. No. 6,168,614 (the entire contents of which are hereby incorporated by reference) issued to Andersen et al. In this patent, the prosthetic valve is mounted on a stent that is collapsed to a size that fits within a catheter. The catheter is then inserted into the patient's vasculature and moved so as to position the collapsed stent at the location of the native valve. A deployment mechanism is activated that expands the stent containing the replacement valve against the valve cusps. The expanded structure includes a stent configured to have a valve shape with valve leaflet supports begins to take on the function of the native valve. As a result, a full valve replacement has been achieved but at a significantly reduced physical impact to the patient.

However, this approach has decided shortcomings. One particular drawback with the percutaneous approach disclosed in the Andersen '614 patent is the difficulty in preventing leakage around the perimeter of the new valve after implantation. Since the tissue of the native valve remains within the lumen, there is a strong likelihood that the commissural junctions and fusion points of the valve tissue (as pushed apart and fixed by the stent) will make sealing around the prosthetic valve difficult. In practice, this has often led to severe leakage of blood around the stent apparatus.

Other drawbacks of the Andersen '614 approach pertain to its reliance on stents as support scaffolding for the prosthetic valve. First, stents can create emboli when they expand. Second, stents are typically not effective at trapping the emboli they dislodge, either during or after deployment. Third, stents do not typically conform to the features of the native lumen in which they are placed, making a prosthetic valve housed within a stent subject to paravalvular leakage. Fourth, stents are subject to a tradeoff between strength and compressibility. Fifth, stents cannot be retrieved once deployed. Sixth, the inclusion of the valve within the stent necessarily increases the collapsed diameter of the stent-valve complex and increases the caliber of the material that must be delivered into the vasculature.

As to the first drawback, stents usually fall into one of two categories: self-expanding stents and expandable stents. Self-expanding stents are compressed when loaded into a catheter and expand to their original, non-compressed size when released from the catheter. These are typically made of Nitinol. Balloon expandable stents are loaded into a catheter in a compressed but relaxed state. These are typically made from stainless steel or other malleable metals. A balloon is placed within the stent. Upon deployment, the catheter is retracted and the balloon inflated, thereby expanding the stent to a desired size. Both of these stent types exhibit significant force upon expansion. The force is usually strong enough to crack or pop thrombosis, thereby causing pieces of atherosclerotic plaque to dislodge and become emboli. If the stent is being implanted to treat a stenosed vessel, a certain degree of such expansion is desirable. However, if the stent is merely being implanted to displace native valves, less force may be desirable to reduce the chance of creating emboli.

As to the second drawback, if emboli are created, expanded stents usually have members that are too spaced apart to be effective to trap any dislodged material. Often, secondary precautions must be taken including the use of nets and irrigation ports.

The third drawback is due to the relative inflexibility of stents. Stents typically rely on the elastic nature of the native vessel to conform around the stent. Stents used to open a restricted vessel do not require a seal between the vessel and the stent. However, when using a stent to displace native valves and house a prosthetic valve, a seal between the stent and the vessel is necessary to prevent paravalvular leakage. Due to the non-conforming nature of stents, this seal is hard to achieve, especially when displacing stenosed valve leaflets.

The fourth drawback is the tradeoff between compressibility and strength. Stents are made stronger or larger by manufacturing them with thicker members. Stronger stents are thus not as compressible as weaker stents. Most stents suitable for use in a valve are not compressible enough to be placed in a small diameter catheter, such as a 20Fr, 16Fr or even 14Fr catheter. Larger delivery catheters are more difficult to maneuver to a target area and also result in more trauma to the patient.

The fifth drawback of stents is that they are not easily retrievable. Once deployed, a stent may not be recompressed and drawn back into the catheter for repositioning due to the non-elastic deformation (stainless steel) or the radial force required to maintain the stent in place (Nitinol). Thus, if a physician is unsatisfied with the deployed location or orientation of a stent, there is little he or she can do to correct the problem.

The sixth drawback listed above is that the combination of the valve within the stent greatly increases the size of the system required to deliver the prosthetic device. As a result, the size of the entry hole into the vasculature is large and often precludes therapy, particularly in children, smaller adults or patients with pre-existing vascular disease.

It is thus an object of the present invention to address these drawbacks. Specifically, it is an object of the invention to provide a support structure that expands gently, with gradual force, thereby minimizing the generation of emboli.

It is further an object of the invention to provide a support structure that traps any emboli generated, thereby preventing the emboli from causing damage downstream.

It is yet another object of the invention to provide a support structure that conforms to the features of the lumen in which it is being deployed, thereby preventing paravalvular leakage.

It is still another object of the invention to provide a strong support structure capable of being deployed from a very small diameter catheter.

It is further an object of the invention to provide a support structure that is capable of being retracted back into a delivery catheter and redeployed therefrom.

It is another object of the invention to provide a device that is delivered with the valve distinctly separated from the inside diameter of the final configuration of the support structure in order to reduce the amount of space required to deliver the device within the vasculature of the patient.

BRIEF SUMMARY OF THE INVENTION

The present invention accomplishes the aforementioned objects by providing a tubular mesh support structure for a native lumen that is capable of being delivered via a very small diameter delivery catheter. The tubular mesh is formed one or more fine strands braided together into an elongate tube. The strands may be fibrous, non-fibrous, multifilament, or monofilament. The strands exhibit shape memory such that the elongate tube may be formed into a desired folded shape, then stretched out into a very small diameter, elongated configuration. The small diameter, elongated configuration makes a very small diameter delivery catheter possible.

Upon deployment, the elongated tube is slowly pushed out of the delivery catheter, where it gradually regains its folded, constructed configuration. The tube conforms to the internal geometries of the target vessel. In addition, the braid effectively traps all emboli that may be released from the vessel walls.

As the tube continues to be pushed from the delivery catheter, it begins to fold in upon itself as it regains its constructed configuration. As it folds in upon itself, the forces exerted by each layer add together, making the structure incrementally stronger. Thus, varying levels of strength may be achieved without changing the elongated diameter of the device.

Using this folded tube, the valve can be attached such that the valve or other structure (such as a filter) in its elongated configuration within the delivery catheter does not reside within the elongated tube, but on deployment can be positioned in, above or below the tube.

BRIEF DESCRIPTION OF THE DRAWINGS

FIG. 1 is a perspective view of a preferred embodiment of the present invention in an elongate configuration;

FIG. 2 is a side view of a preferred embodiment of the present invention;

DETAILED DESCRIPTION OF THE INVENTION

Figure 3:
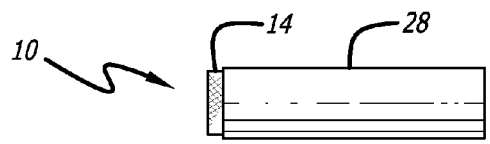
FIGS. 3-12 are a sequence of perspective views of a preferred embodiment of the present invention being deployed from a delivery catheter.
Figure 4:
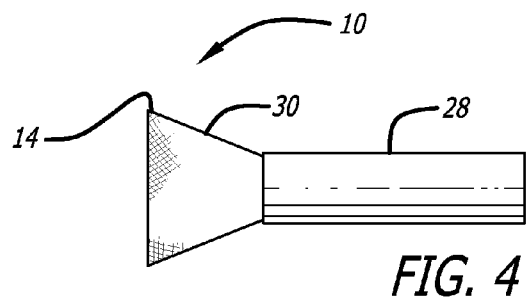
Figure 5:
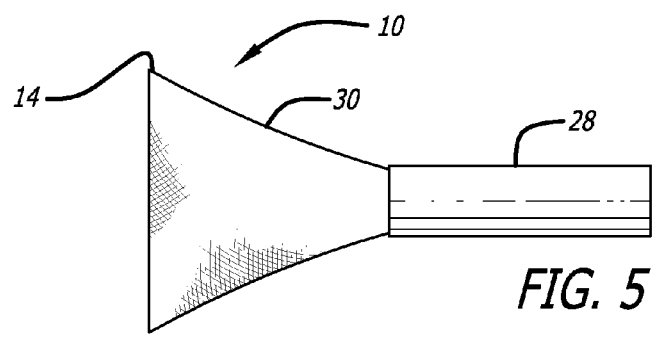
Figure 6:
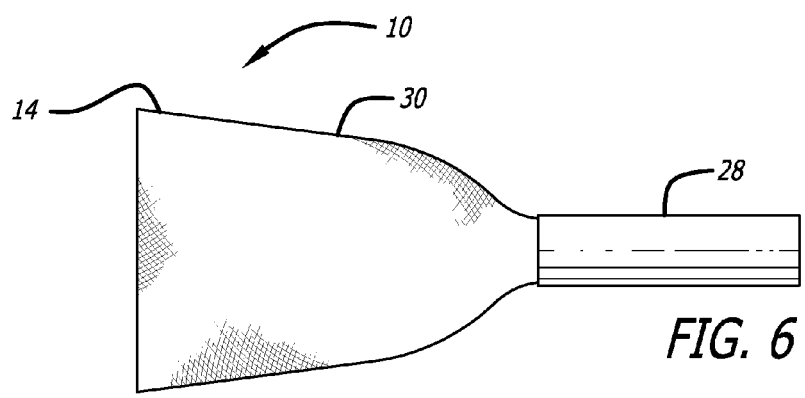

Referring now to the Figures and first to FIG. 1, there is shown a stentless support structure 10 of the present invention in an extended configuration. The valve support 10 includes a first end 12, a second end 14 and an elongate tubular body 16 extending between the first end 12 and the second end 14.

The elongate tubular body 16 is preferably formed from one or a plurality of braided strands 18. The braided strands 18 are strands of a super-elastic or shape memory material such as Nitinol. The strands are braided to form a tube having a central lumen 20 passing therethrough.

In one embodiment, the tubular body 16 is folded in half upon itself such that the second end 14 becomes a folded end and the first end 12 includes a plurality of unbraided strands. The tubular body 16 is thus two-ply. The unbraided strands of the first end 12 are gathered and joined together to form a plurality of gathered ends 22. The gathered ends 22 may be used as commissural points for attaching a prosthetic valve to the support structure 10. (See, e.g. FIG. 2). Alternatively, as shown in FIG. 1, the gathered ends 22 may be used as attachment points for a wireform 24 defining a plurality of commissural points 26.

Notably, the commissural points 26 are positioned such that, when a valve is attached to the support structure in the extended configuration, the valve is longitudinally juxtaposed with the support structure rather than being located within the support structure. This juxtaposition allows the support structure 10 and valve to be packed into a very small catheter without damaging the delicate valve. This longitudinal juxtaposition may be maintained when the support structure assumes a folded or constructed configuration (see FIG. 19 for example), or the valve may become folded within the support structure.

Figure 7:
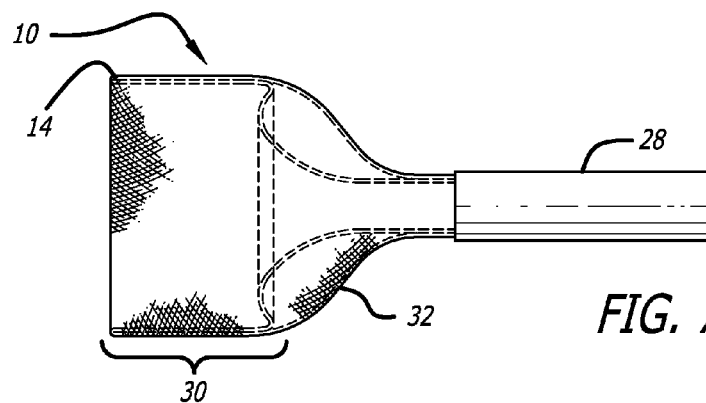
Figure 8:
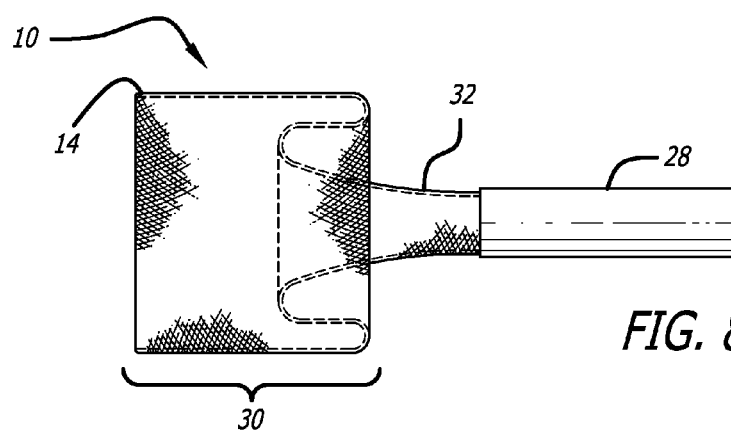
Figure 9:
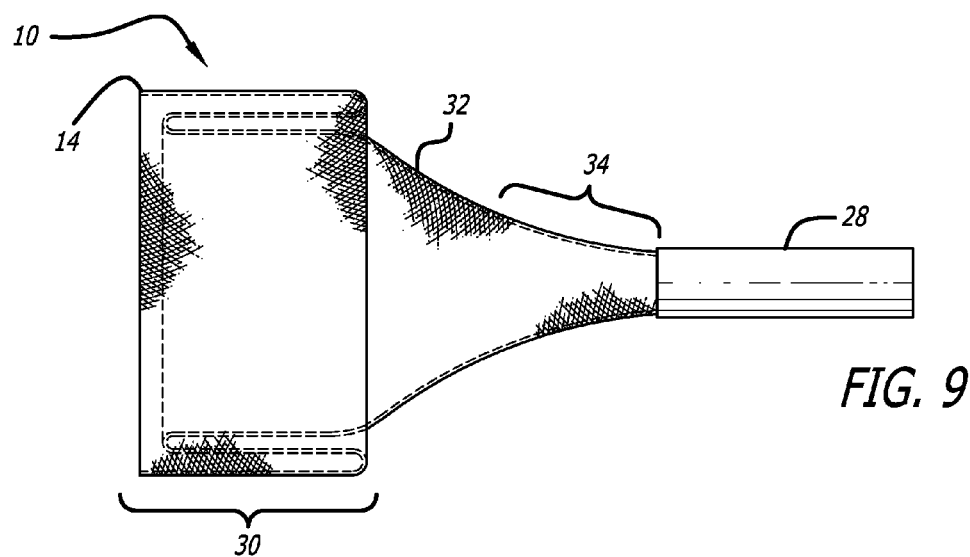

FIGS. 3-6 show the second end 14 emerging from the catheter 28 to expose a first layer 30. In FIG. 7, the first layer 30 is completely exposed and has assumed its constructed configuration. Notably, the first layer 30 contracts longitudinally when fully deployed. Also shown in FIG. 7 is a second layer 32 beginning to emerge from the catheter 28. As the second layer exits the catheter, the pre-set super-elastic fold inverts the mesh, such that a second, inner layer is formed within the first outer layer. Alternatively, the first layer can be deployed against the wall of the vascular structure (such as an artery, vein, valve or heart muscle). As the second layer exits the catheter, the physician can aid inversion of the mesh my advancing the deployment system. In another embodiment, the mesh support structure can be advanced in the vasculature such that it is deployed in a reverse direction (such as deployment through the apex of the heart ventricle or from the venous system), where the mesh inversion occurs as a result of pulling or retracting the deployment system.

Figure 10:
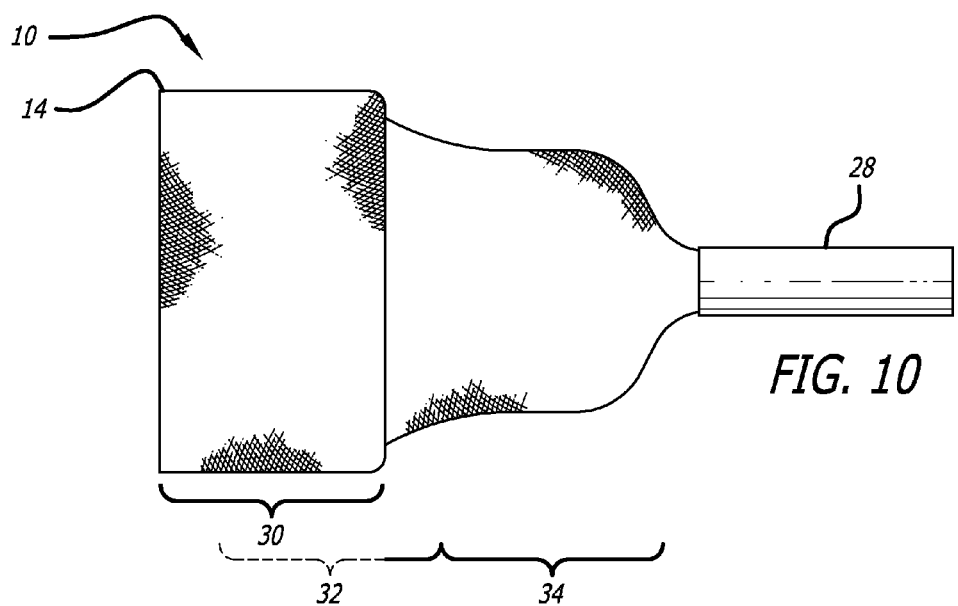
Figure 11:
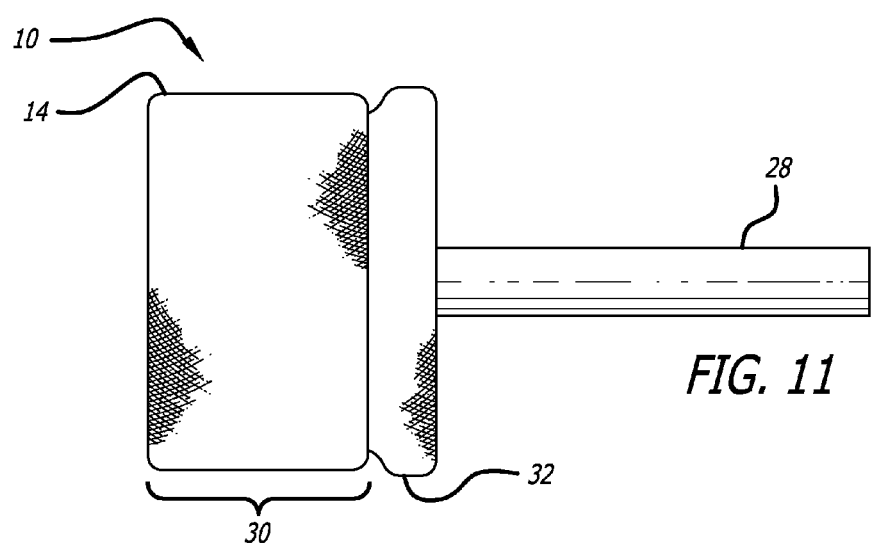

In FIG. 10, the second layer 32 is fully deployed and the third layer 34 is fully exposed, but has not yet been inverted. Retracting the catheter 28, relative to the device 10, while advancing the catheter 28 slightly, relative to the target site, causes the third layer 34 to "pop" inwardly, thereby inverting itself against an inside surface of the second layer 32, as seen in FIG. 11.

Figure 12:
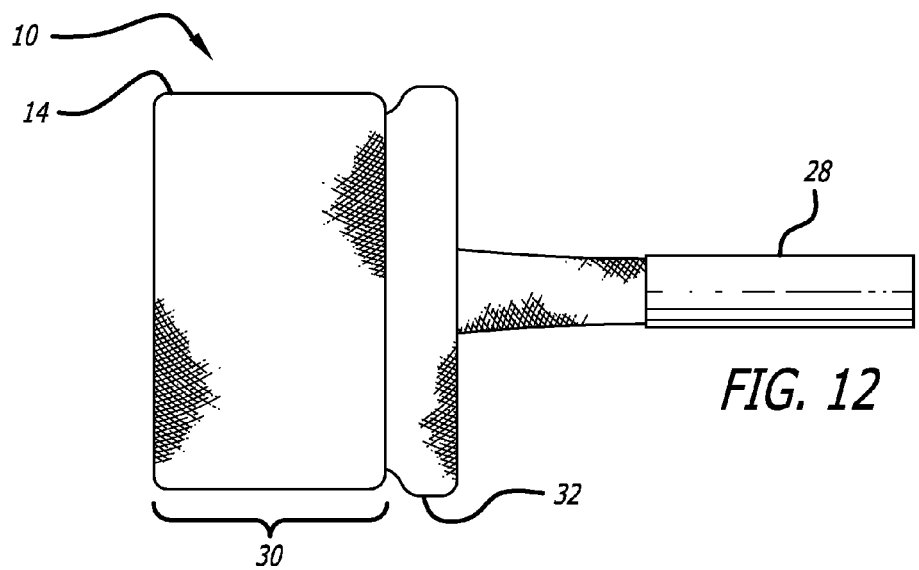

In FIG. 12, additional material has been ejected from the catheter 28 such that the third layer 34 is fully expanded against the second layer. One skilled in the art will realize that numerous additional layers can be achieved in this manner, and that each layer adds additional radial strength to the resulting support structure 10.

Throughout the deployment process, the stentless support structure 10 emerges from the delivery catheter 28 gradually. This characteristic also allows the structure 10 to be pulled back into the delivery catheter 28, in the event that it is desired to relocate the support structure 10. Doing so causes the support structure 10 to reacquire its extended configuration.

Figure 13:
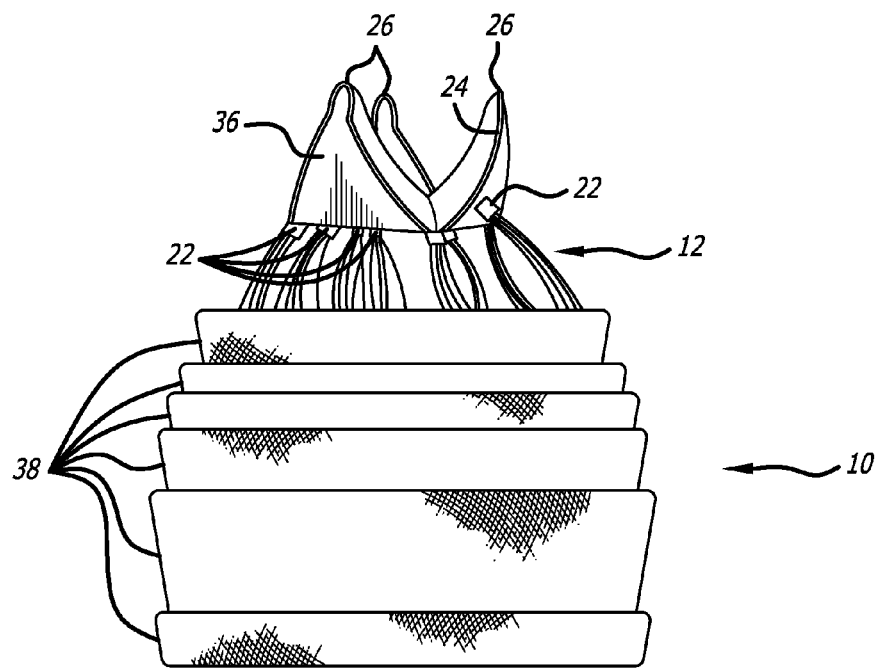
FIG. 13 is a perspective view of a preferred embodiment of the present invention.
Figure 14:
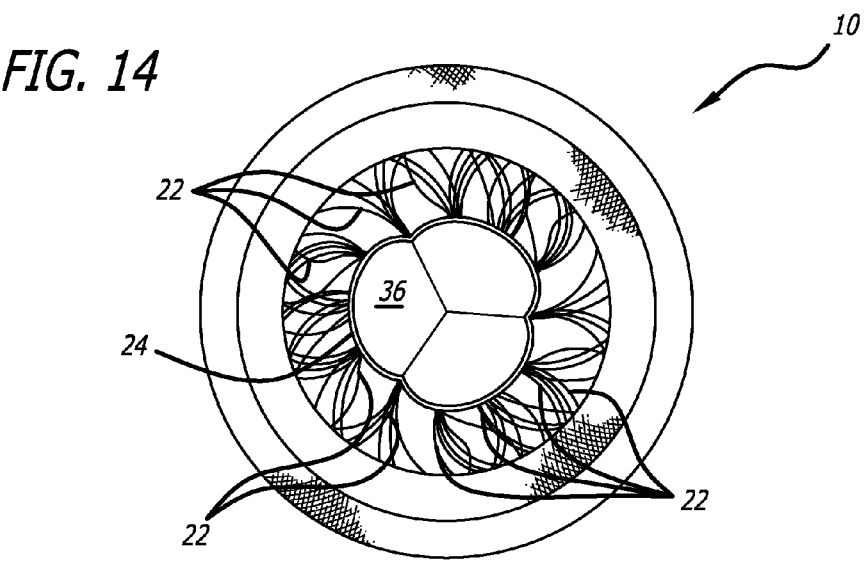
FIG. 14 is a first end view of the preferred embodiment of FIG. 13.
Figure 15:
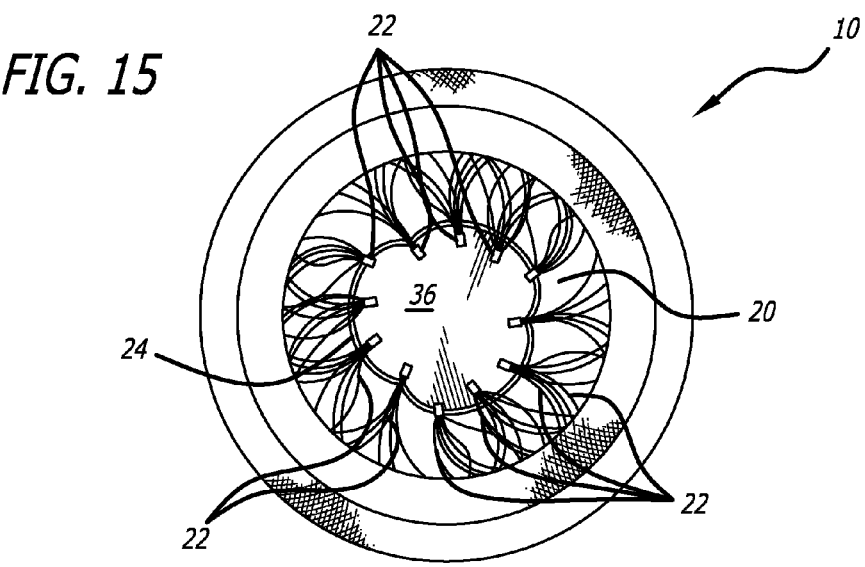
FIG. 15 is a second end view of the preferred embodiment of FIG. 13.

Having described the mechanics of building a support structure in situ, attention can now be turned to various embodiments made possible by the present invention. FIGS. 13-15 show a support structure 10 having many layers 38 and a first end 12 with numerous gathered ends 22 formed from unbraided strands. Some of the gathered ends 22 are attached to a wireform 24 having three commissural points 26. A prosthetic valve 36, either harvested or manufactured, is attached to the wireform 24. FIG. 15 shows the internal lumen 20 of the support structure 10.

Figure 16:
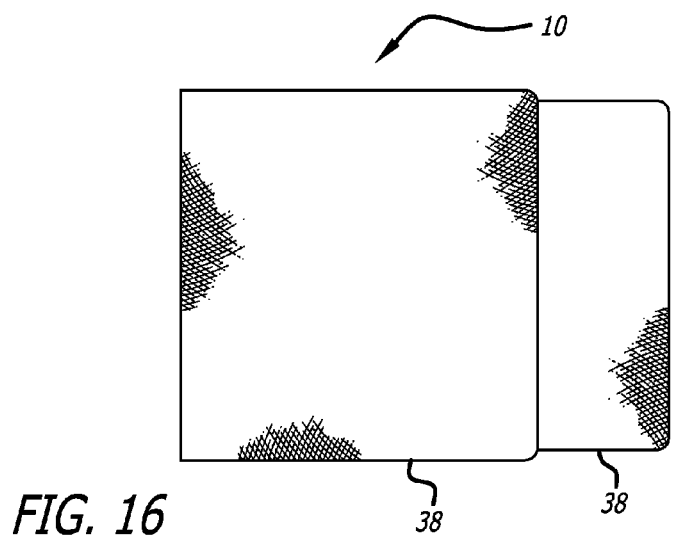
FIG. 16 is a side view of a preferred embodiment of the present invention.
Figure 17:
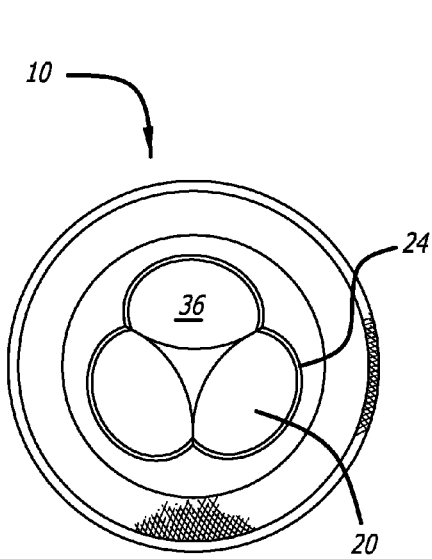
FIG. 17 is a second end view of the preferred embodiment of FIG. 16.
Figure 18:
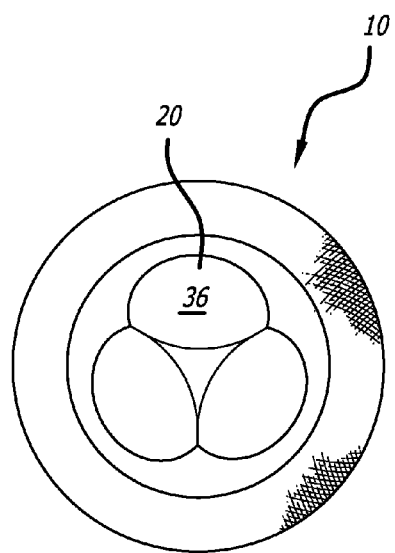
FIG. 18 is a first end view of the preferred embodiment of FIG. 16.

FIGS. 16-18 show a support structure 10 having fewer layers 38 and a wireform 24 with a prosthetic valve 36 attached thereto. The first end 12 (hidden), to which the wireform 24 is attached, has been preformed to fold inwardly upon deployment. Thus, the wireform 24 and prosthetic valve 36, is located in the inner lumen 20 of the support structure 10 when the support structure 10 is in a constructed configuration.

Figure 19:
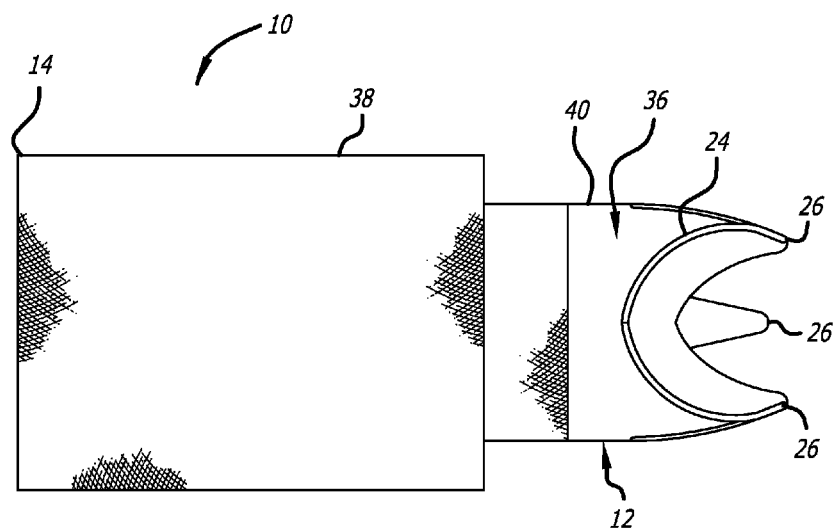
FIG. 19 is a side view of a preferred embodiment of the present invention.
Figures 20, 21:
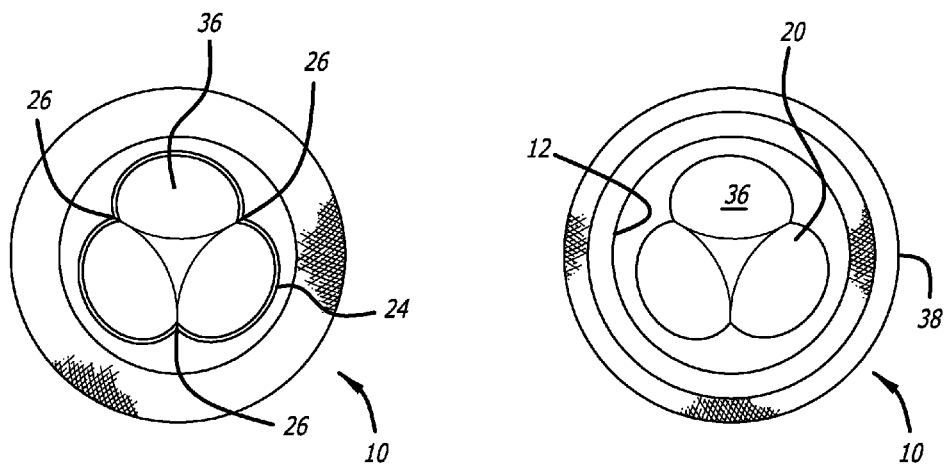
FIG. 20 is a first end view of the preferred embodiment of FIG. 19.
FIG. 21 is a second end view of the preferred embodiment of FIG. 19.

FIGS. 19-21 show a support structure 10 with several layers 38 and a first end 12 preformed to have a smaller diameter than the rest of the layers and the second end 14, which is folded. The terminal ends of the braided strands at the first end 12 have not been formed into gathered ends. Rather, the wireform 24 is attached to the braids. The prosthetic valve 36 is attached to the wireform 24 and has skirting tissue 40, which is placed around the outside of the end 12. The skirting tissue 40 may be adhered to the first end 12.

Figure 22:
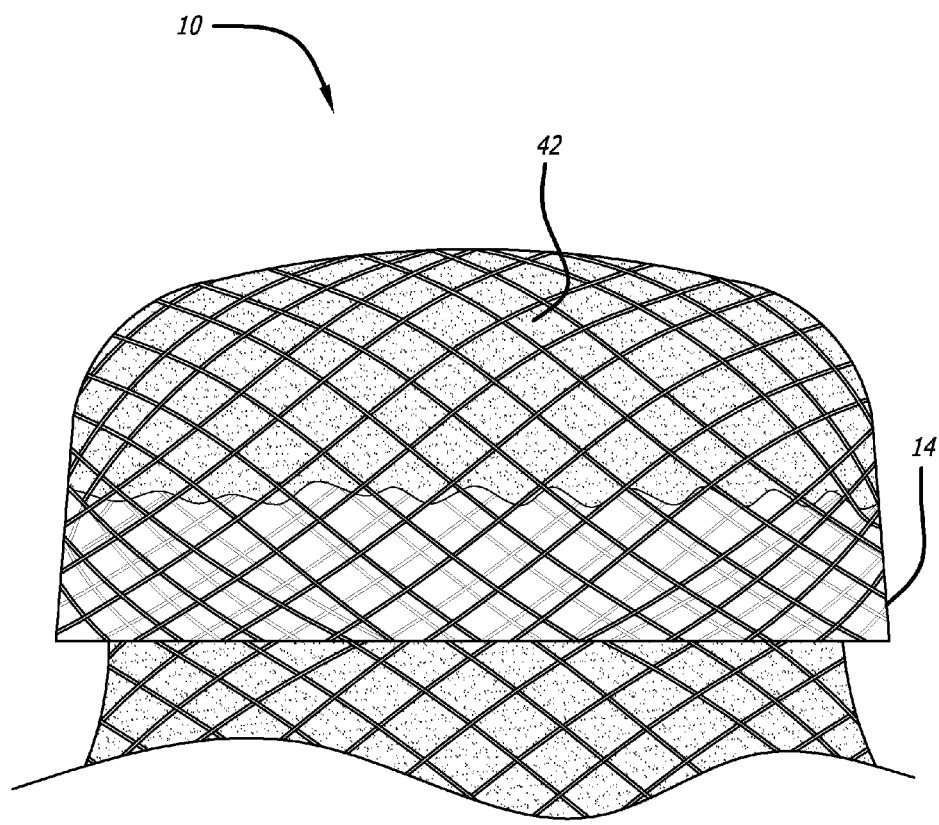
FIG. 22 is a partial perspective view of a preferred embodiment of the present invention.

FIG. 22 shows a stentless support structure 10 with a folded end 14, which has been folded back on itself, and a material 42 trapped between the two layers of the fold. The material 42 is provided to further improve the paravalvular leak prevention and embolic trapping characteristics of the stentless support structure 10. The material 42 could consist of a non-woven material, woven or braided fabric, a polymer or other material.

Figure 23:
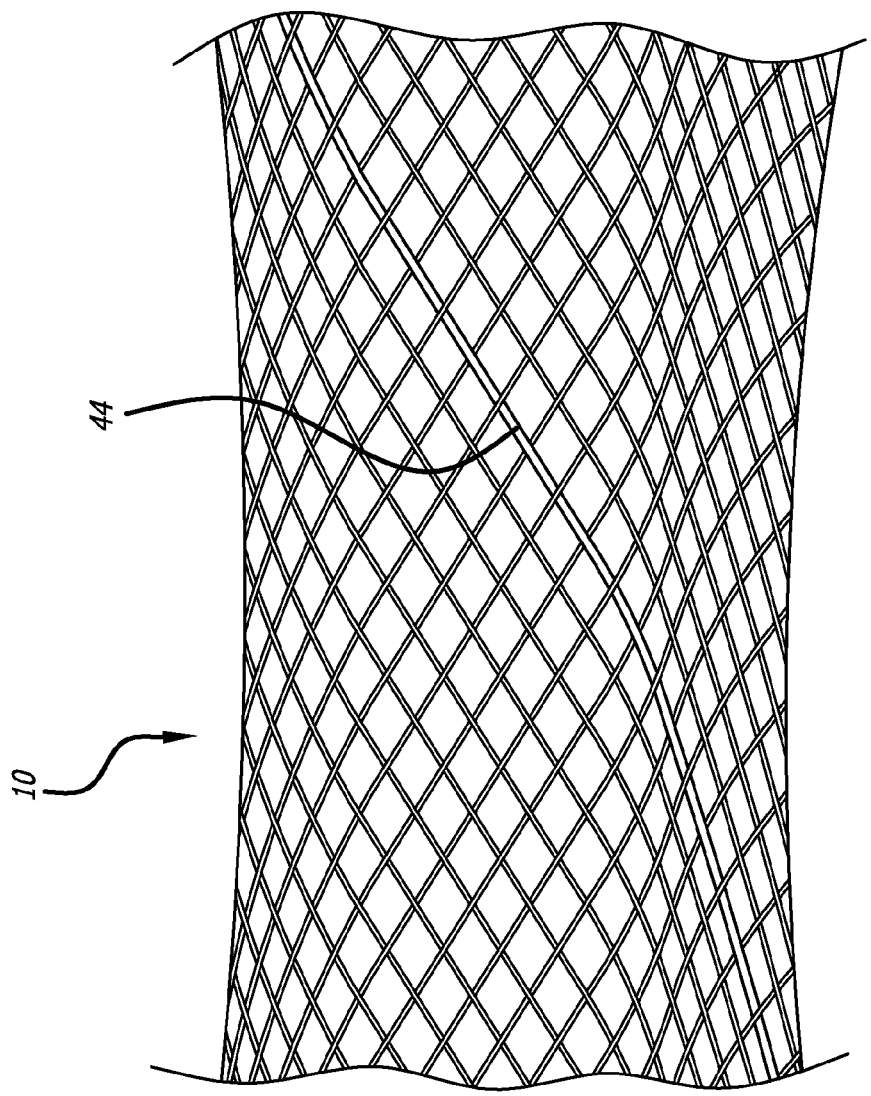
FIG. 23 is a partial perspective view of a preferred embodiment of the present invention.

FIG. 23 shows a stentless support structure 10 that includes a fiber 44 that is larger than the rest of the strands comprising the support structure 10. Thus, FIG. 23 demonstrates that strands of different sizes may be used in the braided support structure 10 without significantly affecting the minimum delivery size of the device. Different sized strands may be used in order to improve strength, provide stiffness, create valve attachment points, provide radiopaque markers, and the like.

Figure 24:
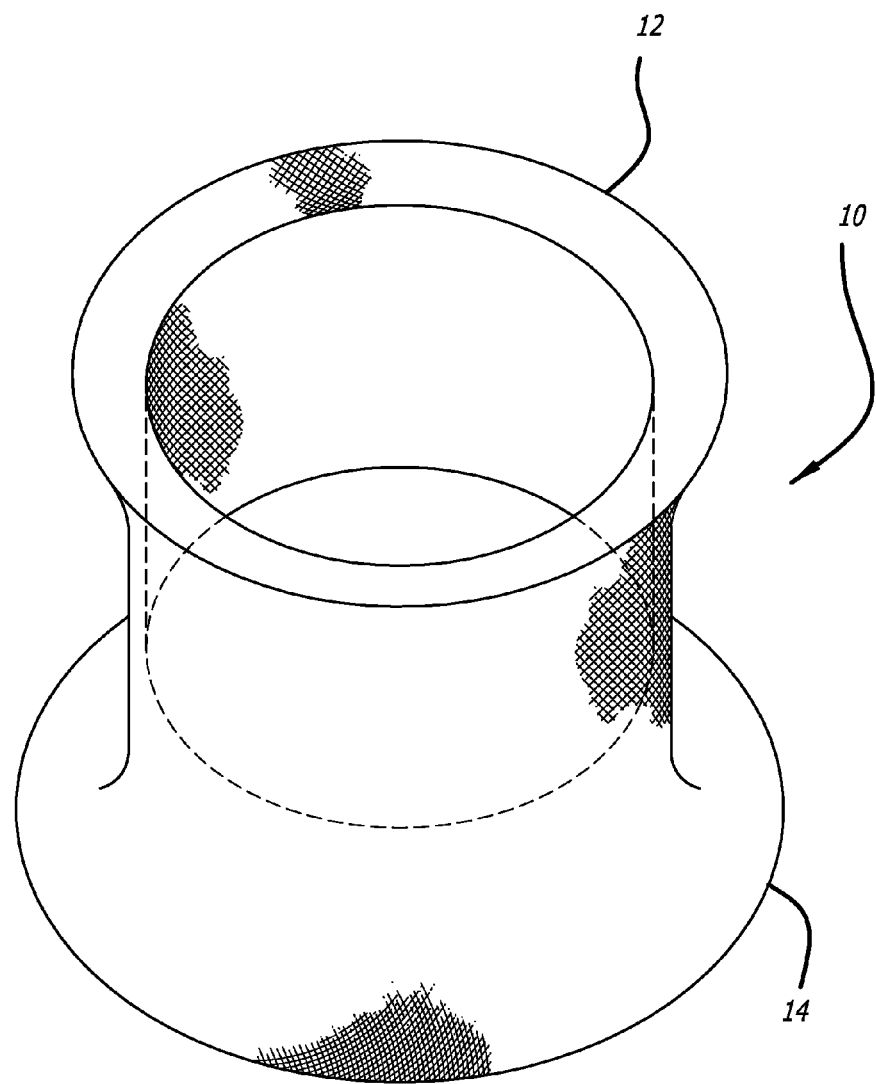
FIG. 24 is a perspective view of a preferred embodiment of the present invention.
Figure 25:
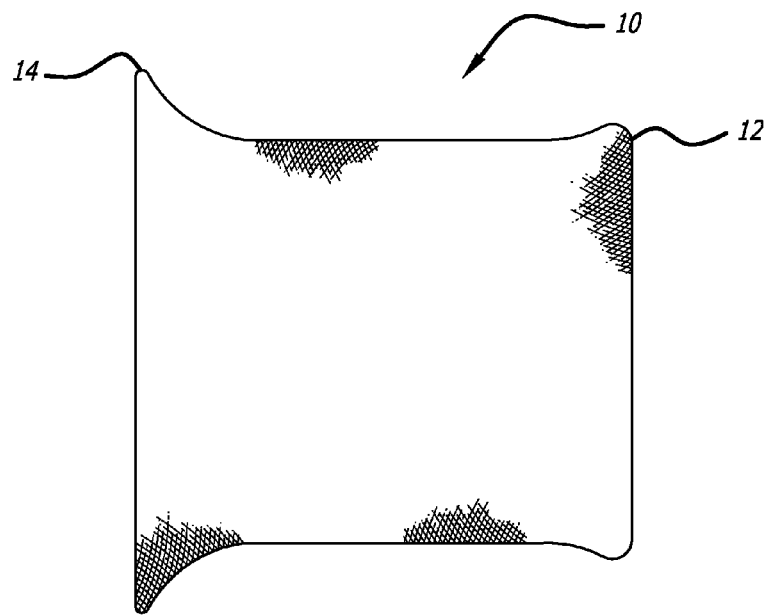
FIG. 25 is a side elevation of the embodiment of FIG. 24.
Figure 26:
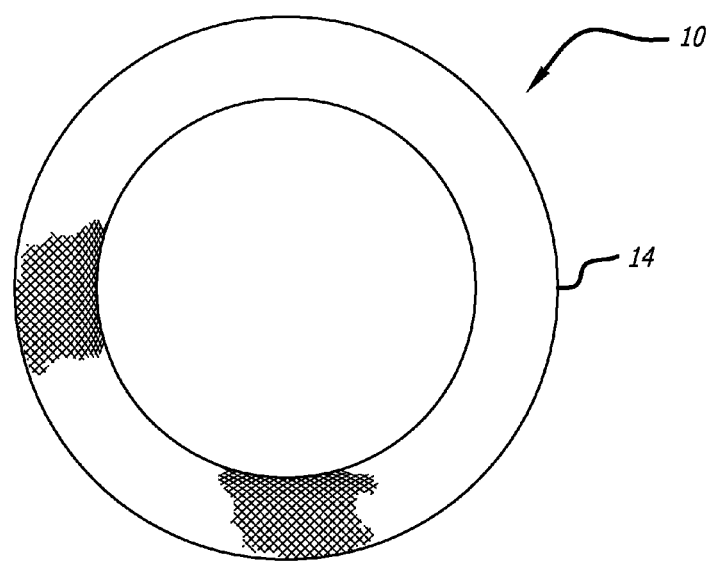
FIG. 26 is a second end view of the embodiment of FIG. 24.

FIGS. 24-26 show a stentless support structure 10 that has a first end 12 that has had the unbraided strands trimmed such that they do not extend past the first end 12 of the folded structure 10. This embodiment may be used to create, preserve or enlarge a lumen. A prosthetic valve may or may not be attached to this embodiment.

Figure 27:
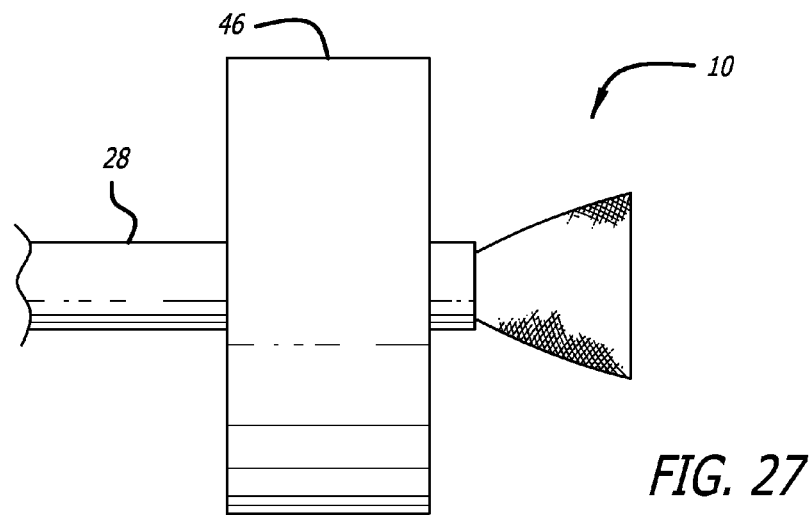
FIGS. 27-36 are a sequence of perspective views of a preferred embodiment of the present invention being deployed from a delivery catheter against a clear plastic tube representing a native valve.

Turning now to FIGS. 27-36, a deployment sequence of a preferred embodiment of the stentless support structure 10 is shown whereby a clear piece of tubing 46 is used to demonstrate a targeted location of a native vessel, such as a native valve. In FIG. 27, the delivery catheter 28 is advanced beyond the targeted valve 46 and the stentless support 10 is starting to be ejected from the catheter 28.

Figure 28:
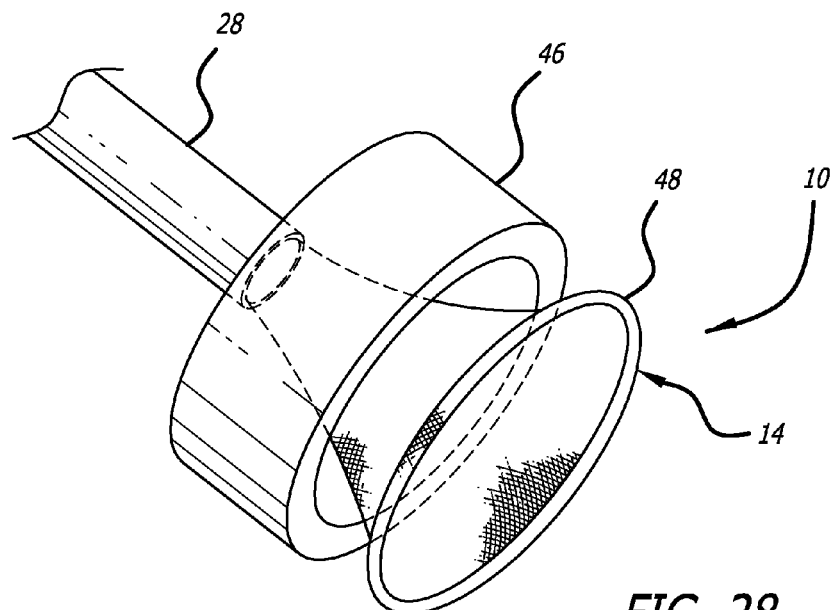
Figure 29:
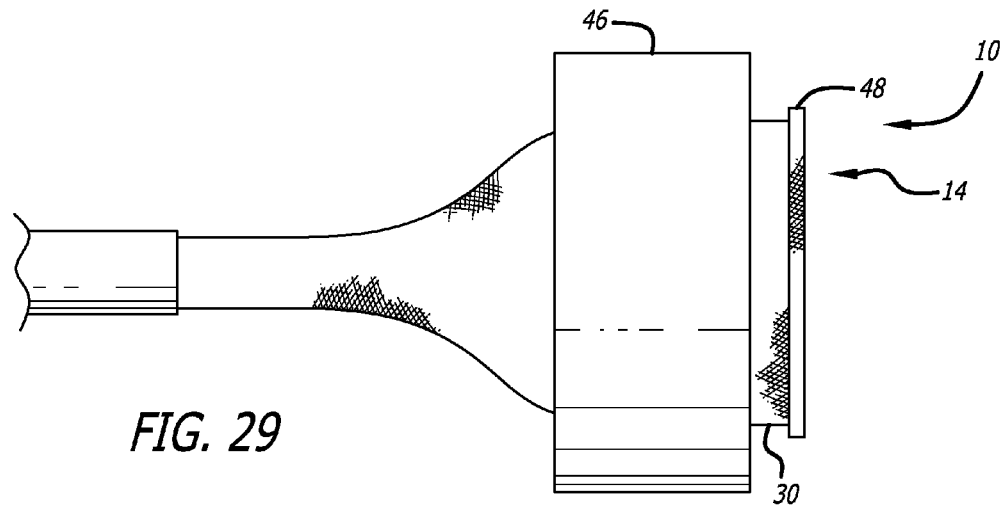

In FIG. 28, enough of the stentless support 10 has been ejected that the second, folded end 14 has begun to curl back on itself slightly, forming a cuff 48. In FIG. 29, the cuff 48 is more visible and has assumed its full, deployed shape. The cuff 48 acts as a catch that a physician can use to visually or tactilely locate the targeted valve 46 and seat the stentless support 10 thereagainst. The cuff also acts to ensure the entire native lumen through the targeted valve 46 is now being filtered by the support 10. Unlike balloon expandable stents, blood flow is not significantly inhibited by the deployment of the stentless support structure 10. Also shown in FIG. 29 is that the first layer 30 has been fully ejected from the catheter 28, as has much of the second layer 32. The first layer 30, being very flexible prior to reinforcement by subsequent layers, is able to conform to any shape of the targeted vessel. The second layer 32 has not yet inverted itself into the first layer 30.

Figure 30:
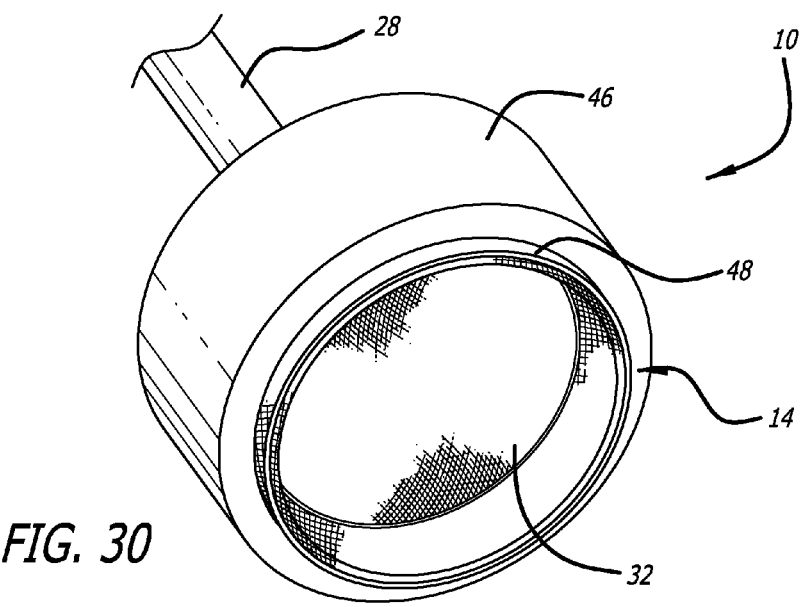
Figure 31:
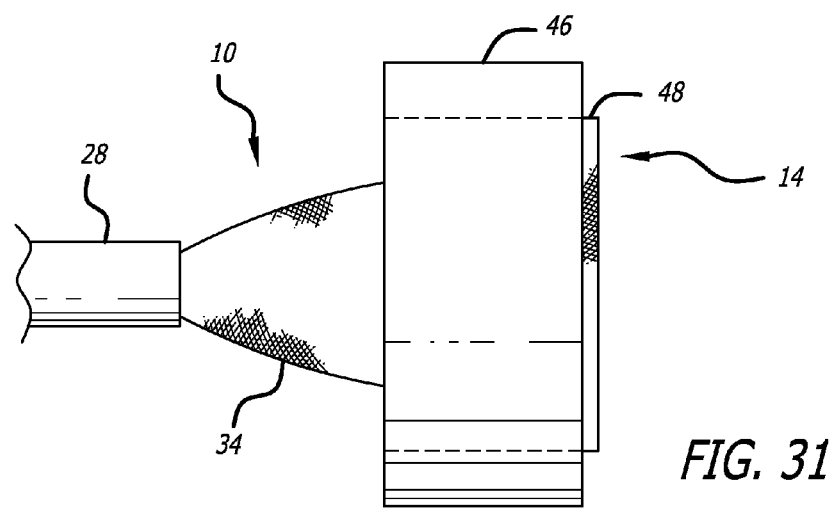

In FIG. 30, the first layer 30 is deployed, the cuff 48 is acting against the valve 46, and the second layer 32 has been inverted. In FIG. 31, material forming the third layer 34 is ejected from the catheter 28 but the third layer 34 has not yet inverted.

Figure 32:
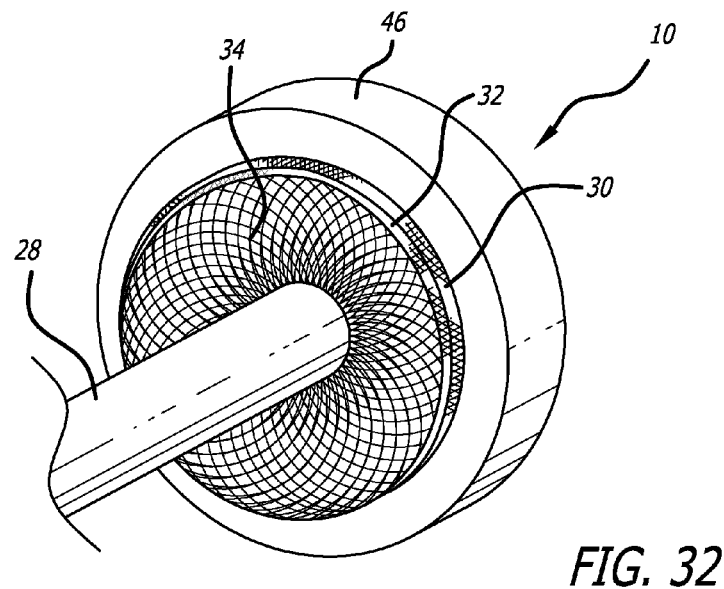
Figure 33:
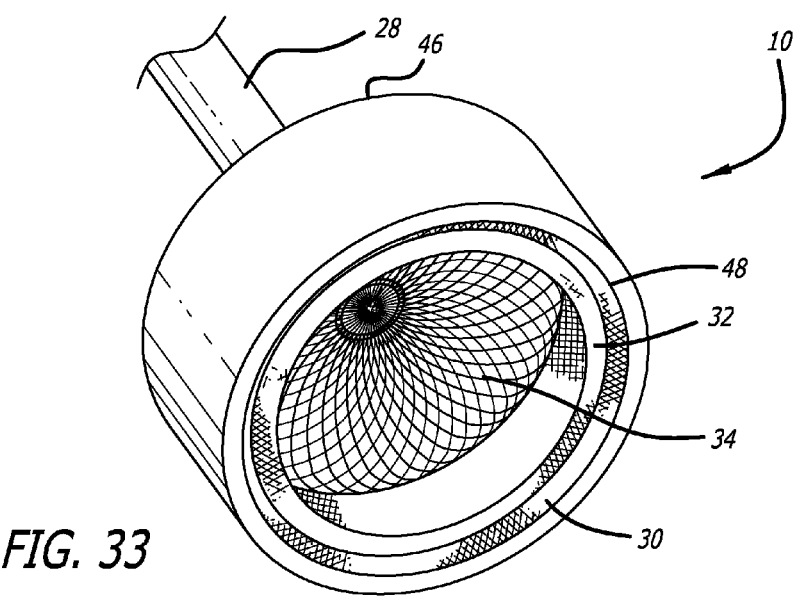

In FIGS. 32-33, the catheter 28 is being advanced to allow the third layer 34 to invert into the second layer 32. The angle of FIG. 32 shows the relatively low profile created by the first and second layers 30 and 32, and how little resistance to blood flow is presented by the support structure 10.

Figure 34:
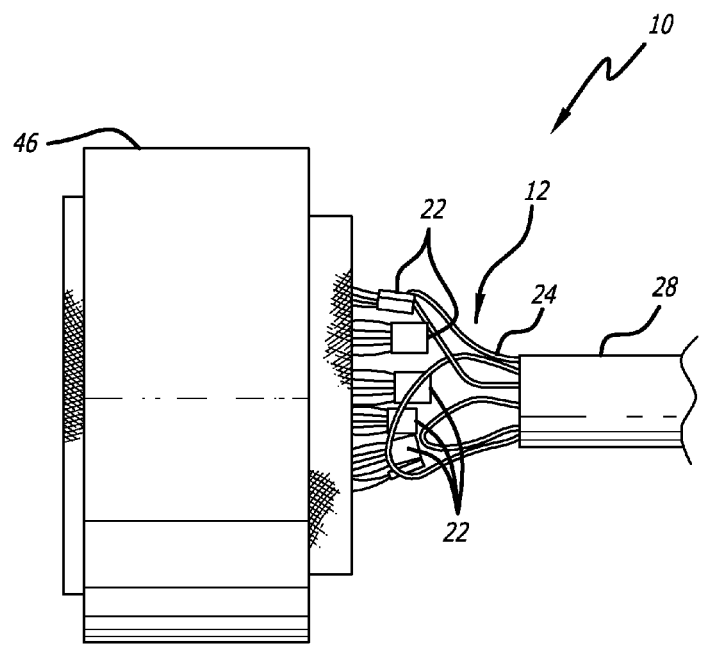
Figure 35:
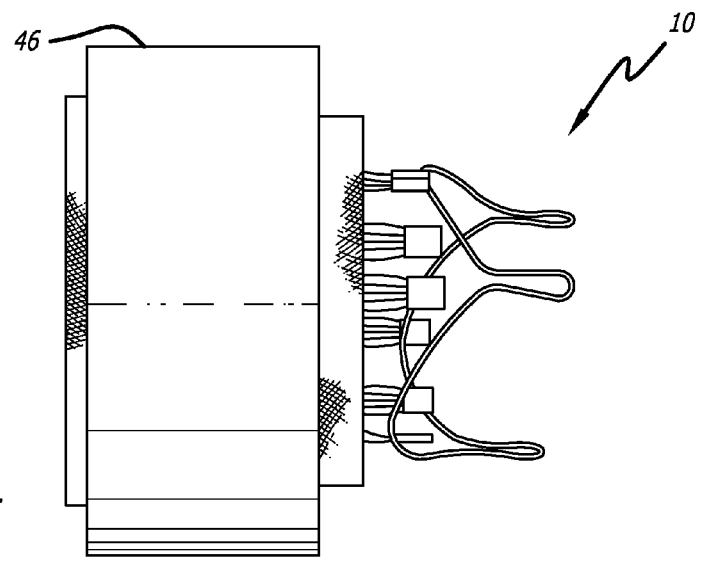
Figure 36:
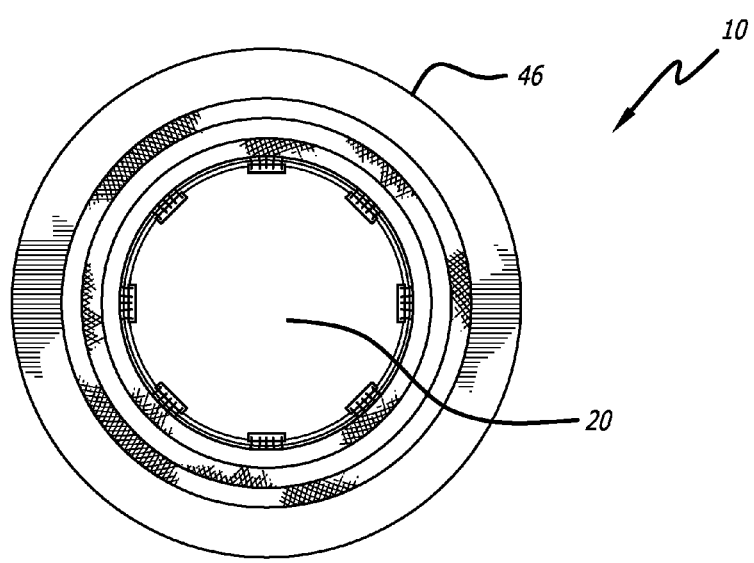

In FIG. 34, the first end 12 has emerged from the catheter 12, and the gathered ends 22 are showing. A wireform 24 is attached to some of the gathered ends 22 and is nearly completely deployed from the delivery catheter 28. In FIGS. 35-36, the support structure 10 has been completely released from the catheter 28. FIG. 36 shows the size of the lumen 20 of the support structure 10.

Figure 37:
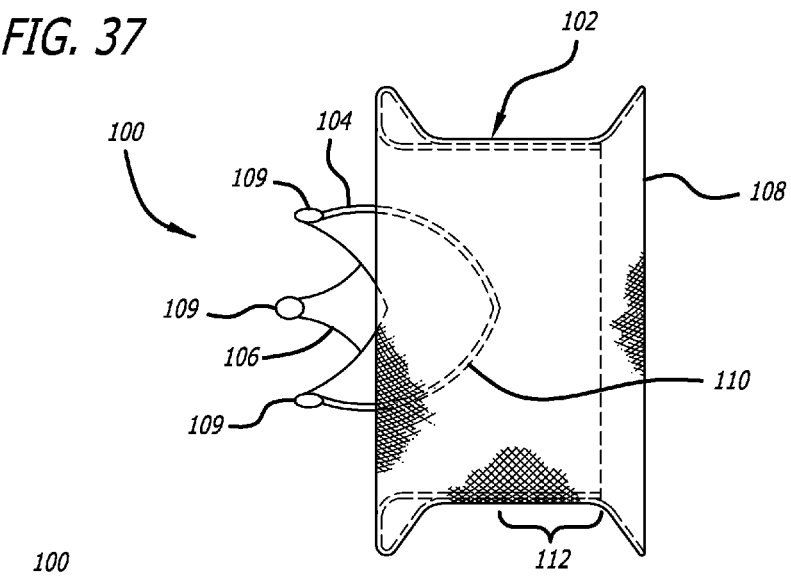
FIG. 37 is a side elevation of a preferred embodiment of the present invention.
Figure 38:
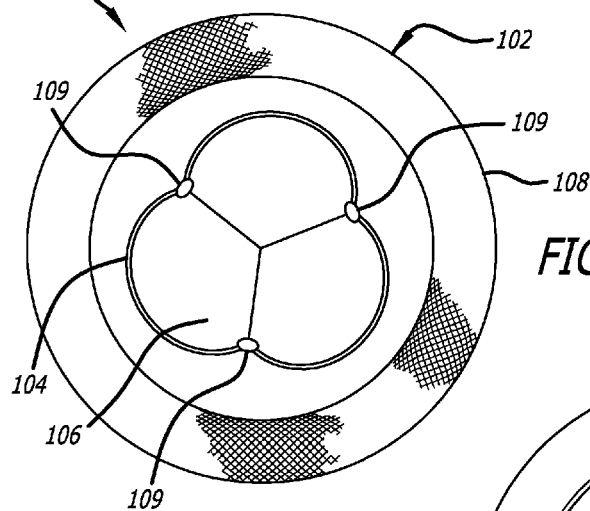
FIG. 38 is an end view of a downstream side of the embodiment of FIG. 37.
Figure 39:
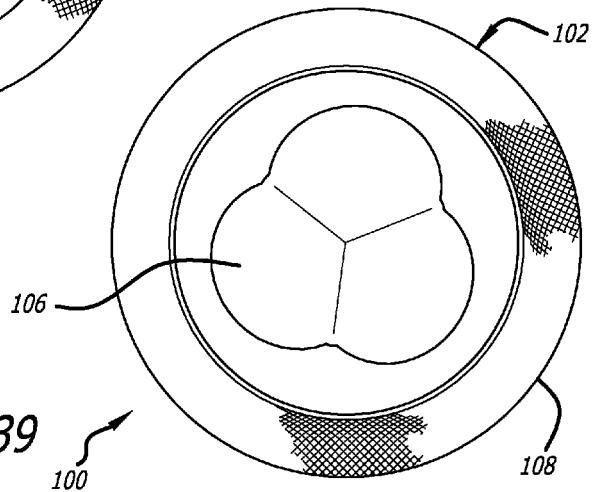
FIG. 39 is an end view of an upstream side of the embodiment of FIG. 37.

FIGS. 37-39 show a preferred embodiment 100 of the present invention including a mesh support structure 102, a wireform 104 and a valve 106. The support structure 102 differs slightly from support structure 10, described previously, as it is constructed from a two individual wires 108. Upon completion of the braiding process, the two free ends of the wire are spliced together. As such, there are no free wire ends and the structure can be loaded into a delivery catheter in a single-ply state (not shown). In the deployed state shown in the Figures, the support structure 102 is folded once to form a two-ply device.

The support structure 102 is preferably formed of a memory alloy such as Nitinol. The single-wire construction allows the device to be compressed into an extremely small catheter, such as one sized 16Fr or smaller. Though the support structure gains rigidity by the two-ply deployed configuration, radial strength is a function of a several factors and can thus be varied widely.

First, as with the other embodiments, radial strength may be increased by incorporating more folds or layers into the deployed configuration of the support structure 102. The three-ply configuration shown in FIGS. 37-39 is the most preferred configuration because it only has to be folded in on itself twice, making deployment less complicated.

Second, strength may be increased by using a heavier wire. Because the support structure 102 is made from a single-wire, and can thus be loaded into a catheter in a single-ply configuration, a larger diameter wire may be used while maintaining a small diameter elongated profile. Support structures 102 have been constructed according to the present invention using single wires having diameters between 0.005 and 0.010 inches in diameter. Preferably, the diameter of the wire is between 0.007 and 0.008 inches.

Third, strength may be increased by increasing the braid density. A tighter braid will result in a stronger support.

Fourth, the strength may be increased by altering the heat setting parameters. Super-elastic and shape memory alloys, such as Nitinol, attain their deployed shape within the vasculature by being heat set. The wires are held in a desired configuration and heated to a predetermined temperature for a predetermined period of time. After the wires cool, they become set to the new configuration. If the wires are later disfigured, they will return to the set configuration upon heating or simply releasing the wires. The force with which a super-elastic or shape memory alloy returns to a set configuration can be increased by modifying the temperature at which the configuration is set, or by modifying the period of time the alloy is maintained at the elevated setting temperature. For example, good results have been attained setting a Nitinol support structure of the present invention at 530° C. for 7 minutes. Stiffer support structures can be made using the same Nitinol wire by setting the structure at a temperature other than 530° C. or by setting the structure at 530° C. for a time other than 7 minutes, or both.

The device 100 includes a wireform 104, to which a valve 106 is attached. The wireform 104 form commissural points 109 separated by arcuate portions 110. The arcuate portions 110 are attached to an inside surface of the support structure 102. The commissural points 109 facilitate natural and efficient opening and closing of the valve 106. Alternatively, the valve commissural points can be attached to an outer surface of the support structure (not shown).

The valve 106 may be any form of prosthetic or harvested biological valve. Preferably, as shown in the Figures, the valve 106 is a valve having three leaflets. The valve 106 is sutured or otherwise attached to the wireform 104. Preferably, the valve 106 is cut or constructed to include a skirt portion 112 which continues along the length of the support structure 102 in its deployed configuration.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A stentless support structure comprising:
    a strand braided to form a tubular structure having an unfolded delivery configuration and a folded delivered configuration;
    whereby in the unfolded delivery configuration, the tubular structure includes:
        a first end and a second end;
        an elongate tubular body between the first end and the second end;
    whereby in the folded delivered configuration, the tubular structure includes:
        at least one circumferential fold in the elongate tubular body reducing a length of the tubular structure and creating a tubular section of the body having at least twice as many layers as the elongate tubular body in the unfolded delivery configuration.

2. A prosthetic valve assembly comprising:
    a tube having a elongated configuration and a folded configuration;
    a wireform defining a plurality of commissural points, said wireform having a distal end;
    a valve attached to said wireform;
    wherein in the elongated configuration, said distal end of said wireform is connected to a proximal end of said tube such that said wireform is longitudinally adjacent to said tube; and,
    wherein in the folded configuration, said proximal end of said tube folds inwardly such that said wireform is at least partly contained within an interior of said tube.

3. The prosthetic valve assembly of claim 2 wherein said tube comprises a mesh structure.

4. The prosthetic valve assembly of claim 2 wherein said wireform comprises three commissural points.

5. The prosthetic valve assembly of claim 2 wherein said wireform comprises connection points between said commissural points that are secured to said end of said tube.

6. The prosthetic valve assembly of claim 2 wherein said valve comprises tissue.

7. The prosthetic valve assembly of claim 2 wherein said valve comprises a skirt that overlaps said end of said tube.

8. The prosthetic valve assembly of claim 2 further comprising fabric secured to an inside surface of another end of said tube opposite said wireform, such that, in said folded configuration, said fabric becomes interposed between two layers of said tube.

9. The prosthetic valve assembly of claim 2 wherein said valve is sewn to said wireform.

10. The prosthetic valve assembly of claim 2 wherein said wireform comprises Nitinol.

11. The prosthetic valve assembly of claim 2 wherein said tube comprises at least one preformed fold enabling said folded configuration when released.

12. A prosthetic valve assembly comprising:
a tube having a elongated configuration and a folded configuration;
an annular wireform defining a plurality of commissural points, an end of the wireform being connected to an end of the tube;
a valve attached to said wireform;
wherein in the elongated configuration, said wireform is substantially outside of said tube; and,
wherein in the folded configuration, said wireform is at least partly contained within an interior of said tube.

13. The prosthetic valve assembly of claim 12 wherein said tube comprises a mesh structure.

14. The prosthetic valve assembly of claim 12 wherein said wireform comprises three commissural points.

15. The prosthetic valve assembly of claim 12 wherein said wireform comprises connection points between said commissural points that are secured to said end of said tube.

16. The prosthetic valve assembly of claim 12 wherein said valve comprises tissue.

17. The prosthetic valve assembly of claim 12 wherein said valve comprises a skirt that overlaps said end of said tube.

18. The prosthetic valve assembly of claim 12 further comprising fabric secured to an inside surface of another end of said tube opposite said wireform, such that, in said folded configuration, said fabric becomes interposed between two layers of said tube.

19. The prosthetic valve assembly of claim 12 wherein said valve is sewn to said wireform.

20. The prosthetic valve assembly of claim 12 wherein said tube comprises at least one preformed fold enabling said folded configuration when released.

* * * * *